(12) United States Patent
Nakashima et al.

(10) Patent No.: US 6,627,964 B2
(45) Date of Patent: Sep. 30, 2003

(54) GAS SENSOR

(75) Inventors: Kenshiro Nakashima, Aichi (JP); Yasuo Okuyama, Aichi (JP); Hitoshi Yokoi, Aichi (JP); Takafumi Oshima, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 09/924,551

(22) Filed: Aug. 9, 2001

(65) Prior Publication Data

US 2002/0020853 A1 Feb. 21, 2002

(30) Foreign Application Priority Data

Aug. 10, 2000 (JP) ........................ 2000-242029
Dec. 8, 2000 (JP) ........................ 2000-374551

(51) Int. Cl.[7] .............................. H01L 29/66
(52) U.S. Cl. .................. 257/414; 257/77; 257/769; 257/565
(58) Field of Search .................. 257/414, 77, 769, 257/565

(56) References Cited

U.S. PATENT DOCUMENTS

| 4,058,368 A | 11/1977 | Svensson et al. |
|---|---|---|
| 4,836,012 A | 6/1989 | Doty et al. |
| 5,362,975 A | 11/1994 | von Windheim et al. |
| 5,698,771 A | 12/1997 | Shields et al. |
| 5,710,059 A | 1/1998 | Rottner |
| 5,929,523 A | 7/1999 | Parsons |
| 6,109,094 A | 8/2000 | Baranzahi et al. |
| 6,150,246 A | 11/2000 | Parsons |
| 6,291,838 B1 * | 9/2001 | Hunter .................. 257/76 |

FOREIGN PATENT DOCUMENTS

| JP | 54-87291 | 7/1979 |
|---|---|---|
| JP | 6-222027 | 8/1994 |
| JP | 10-505911 | 6/1998 |
| JP | 2000-101064 | 4/2000 |
| JP | 2000-150417 | 5/2000 |
| WO | 56-142445 A | 11/1981 |
| WO | WO 96/09534 A1 | 3/1996 |

OTHER PUBLICATIONS

"Effect of Si or Al Interface Layers on the Properties of Ta and Mo Contacts to p–Type SiC," *Journal of Electronic Materials*, vol. 29, No. 3, 2000, pp. 391–397.
"Movement of Advanced Microsensor Process Technologies", IEEJ Technical Report, No. 727, pp. 18–22, 1999.
"Dry Etching of SiC Surface", Proceedings of 60th Annual Meeting of JSAP, No. 1, 3p–R–1, p. 335, 1999.
"Development Trend of Single Crystal Growth Technology for SiC Bulk", Electronic Materials, pp. 57–62, Nov. 1998.
European Search Report for EP 01 30 6801 dated May 22, 2003.
J.P. Lukaszewicz, "An Application of Carbon–type Semiconductors for the Construction of a Humidity–sensitive Diode", *Sensors and Actuators*, Jan. 1992, vol. B6, pp. 61–65.

* cited by examiner

*Primary Examiner*—Jerome Jackson
(74) *Attorney, Agent, or Firm*—Sughrue Mion, PLLC

(57) ABSTRACT

A gas sensor having a pn junction including two discrete electrical conductive-type layers, namely, a first semiconductor layer and a second semiconductor layer, disposed in contact with each other. Ohmic electrodes are formed on the respective surfaces of the semiconductor layers. A catalytic layer containing a metallic catalytic component which dissociates hydrogen atom from a molecule having hydrogen atom is formed on one of the ohmic electrodes. The pn junction diode-type gas sensor has a simple constitution, exhibits a small change in diode characteristics with time in long-term service and is capable of detecting a gas concentration of a molecule having a hydrogen atom, for example, $H_2$, $NH_3$, $H_2S$, a hydrocarbon and the like, contained in a sample gas.

8 Claims, 8 Drawing Sheets

GAS SENSOR

BACKGROUND OF THE INVENTION

1. Field of the Invention

The present invention relates to gas sensors for detecting concentrations of $H_2$, $NH_3$, $H_2S$, hydrocarbons and the like included in sample gases and, particularly, to a gas sensor using a pn junction diode as a detecting device. The sensor of the present invention is preferably adapted for detecting leakage of hydrogen from a fuel cell and the like, controlling or monitoring an ammonium selective reduction catalyst for use in a power plant, a co-generation system and the like, or monitoring a three way catalyst or an NOx adsorption catalyst and the like of an automotive vehicle.

2. Description of the Related Art

Gas sensors in which oxide semiconductors serve as detecting elements have been used for measuring concentrations of sample gases having hydrogen atoms, hydrocarbons and the like. One measurement principle is to detect an increase in conductivity caused by electron transport from a molecule having a hydrogen atom and the like adsorbed in an oxide semiconductor as a change in voltage. As an example, Japanese Patent Laid-Open No. 87291/1979 discloses a gas sensor in which an oxide semiconductor thin layer is formed on a surface of a pn junction diode via a dielectric thin layer.

However, the gas sensor employing an oxide semiconductor as a detecting element is provided with a heater for activating the oxide semiconductor. When a highly inflammable gas such as hydrogen and the like is used, there is a possibility of fire upon contact with the heater due to gas leakage. For this reason, as in the case of a fuel cell and the like, it is not preferable to use a gas sensor employing an oxide semiconductor as a detecting element in a system containing a highly inflammable a gas such as hydrogen and the like. Further, in the above case, there is another problem of large electricity consumption because of the need for powering the heater.

A gas sensor which uses a diode fabricated by finely processing a semiconductor has been studied as a detecting element which does not require a heater. A gas sensor based on a Shottky diode, a MIS (Metal-Insulator-Semiconductor) diode, a FET (Field Effect Transistor) diode or the like which utilizes a change in the rectification characteristics of a semiconductor due to absorption of sample gas components has been proposed. The measurement principle involves measuring a change in potential of the diode in a dipole layer caused by an adsorbed sample gas in an electrode layer having a catalytic effect.

International Patent Publication No. 505911/1998 discloses a gas sensor using an MIS-type diode having improved long-term stability and response by providing an intermediate layer such as $TaSi_x$ and the like in an electrode layer having catalytic activity to a sample gas. Japanese Patent Laid-Open No. 222027/1994 discloses a Shottky diode type gas sensor using diamond as a semiconductor.

Recently, various types of gas sensors in which SiC (silicon carbide) is used as a semiconductor have been investigated. SiC is more advantageous than Si in its voltage breakdown characteristics, response time and the like. Further, since Si has a band gap of about 1.1 eV, Si can not be used under circumstances in which the temperature is over 150° C. In contrast, since SiC has a large band gap of about 2.2 eV to about 3.3 eV (3C—SiC, 6H—SiC and 4H—SiC have band gaps of 2.23 eV, 3.03 eV and 3.26 eV, respectively where C represents cubic; H represents hexagonal and wherein the numerals, for example, 3, 4, 6 and the like, before C and H represent recurring periods of a crystal structure), SiC is advantageous in that it can be used even at a high temperature of about 600° C. For this reason, SiC is expected to be applied to a gas sensor which can be operated even at a high temperature.

A Shottky diode-type gas sensor has been studied at NASA Lewis Research Center. Further, a capacitor type or a shottky diode-type sensor has been studied at Linkong University, Sweden (Movement of Advanced Microsensor Process Technologies, IEEJ Technical Report, No. 727, pp. 18–22, 1999).

On the other hand, it is known that a surface of a SiC single crystal wafer has a surface-roughness on the order of nanometers (Proceedings of 60th Annual Meeting of JSAP, No. 1, 3p-R-1, p. 335, 1999). Further, it is known that a hollow through-hole called a "micropipe defect" is liable to be generated (Electronic Materials, pp. 57–61, November, 1998).

In order to fabricate a gas sensor using a SiC single crystal, strict process control is necessary so as to avoid the influence of surface roughness or a surface defect such as a micropipe and the like on the SiC single crystal.

Further, there is a concern of a change in diode characteristics of the Shottky diode-type gas sensor with time in long-term service under a high-temperature condition due to deterioration of the state of an interface between an electrode and a Shottky contact of a semiconductor. This change with time in long-term service is also a concern in the case employing a Si single crystal.

SUMMARY OF THE INVENTION

It is therefore an object of the present invention to provide a gas sensor having a simple structure, exhibiting a small change of diode characteristics with time in long-term service in which either a Si single crystal or SiC single crystal is employed, and which is capable of detecting the concentration of a gas containing a molecule having a hydrogen atom, for example, $H_2$, $NH_3$, $H_2S$, a hydrocarbon and the like.

Accordingly, the present invention provides a pn junction diode-type gas sensor comprising:

- a first semiconductor layer which is either a p-type or n-type semiconductor layer;
- a second semiconductor layer of a type different from said first semiconductor layer;
- a semiconductor substrate on which said first semiconductor layer and said second semiconductor layer are disposed;
- a first ohmic electrode in electrical contact with said first semiconductor layer;
- a second ohmic electrode in electrical contact with said second semiconductor layer; and
- a catalytic layer containing a metallic catalytic component disposed on one of said first ohmic electrode and said second ohmic electrode, said catalytic component dissociating hydrogen atom from a molecule having hydrogen atom in contact with the catalytic layer.

The pn junction diode-type gas sensor of the present invention comprises a catalytic layer containing a metallic catalytic component which dissociates hydrogen atom from a molecule having hydrogen atom. The catalytic layer is disposed on an ohmic electrode which works as a detection electrode. By using such a pn junction diode as a detecting element, it becomes possible to detect the concentration of a gas containing a molecule having a hydrogen atom. Ordinarily, the Shottky diode-type gas sensor could not obtain rectifying characteristics unless a thin, uniform electrical insulating film having a thickness of about 1 nm to about 10 nm was formed between the semiconductor and the electrode. When a defect is present in the electrical insulating film, a dielectric breakdown over time in long-term service will occur. However, it is very difficult to industrially prepare a thin, uniform film having a thickness of about 1 nm to 10 nm whereupon the production cost of the Shottky diode-type gas sensor becomes high. Particularly, this is conspicuous when SiC which is liable to have a defect such as a micropipe and the like therein is used as a semiconductor. In contrast, the pn junction diode-type gas sensor of the present invention does not always require an electrical insulating film of $SiO_2$ or the like between the semiconductor and the electrode unlike the Shottky diode-type gas sensor. Under these circumstances, the pn junction diode-type gas sensor has the advantage of lower production cost than a Shottky diode-type gas sensor even when a compound semiconductor substrate such as SiC which is liable to contain a defect such as a micropipe is employed therein. Further, since dielectric breakdown of the electrical insulating film under a high temperature condition is prevented, the gas sensor employing the pn junction-type diode as the detecting element has excellent reliability. By using the pn junction-type diode as the detecting element, it becomes possible to fabricate a gas sensor which hardly suffers from a change in diode characteristics with time over long-term service and has excellent ambient resistance.

The "ohmic electrode which works as a detection electrode" referred to herein denotes an ohmic electrode which can detect a voltage shift that is generated when the current is held constant as an electrical signal, in the current-voltage characteristics of the semiconductor in which a pn junction is formed. In other words, it represents an ohmic electrode which can detect a concentration of a molecule having a hydrogen atom contained in a sample gas. Contact-potential difference based on work function difference derived from contact with a molecule having a hydrogen atom is generated between the semiconductor and the electrode. When an electrode having a smaller work function value than that of an n-type semiconductor is selected or an electrode having a work function value greater than that of a p-type semiconductor is selected, an ohmic electrode having an ohmic junction can be obtained. Further, the gas sensor of the present invention forms a pn junction in which a first semiconductor layer and a second semiconductor layer contact each other.

The mechanism of detecting the concentration of a molecule having a hydrogen atom contained in a sample gas is described below using a gas sensor of the present invention. A contact-potential difference based on work function difference is generated between the semiconductor and the ohmic electrode by contacting a molecule having a hydrogen atom and, subsequently dissociating the hydrogen atom therefrom. In other words, a contact-potential difference proportional to a dissociated hydrogen concentration is generated by an effect of the thus dissociated hydrogen atom. In accordance with this change, a voltage change entails so as to maintain constant current flow. This voltage shift is detected as an electrical signal corresponding to the concentration of a molecule having a hydrogen atom contained in a sample gas.

When an ohmic electrode capable of detecting the concentration of a gas containing a molecule having a hydrogen atom is formed on a surface of an n-type layer which in turn is formed on a p-type semiconductor, as shown in FIG. 3, the voltage shifts in an increasing direction. FIG. 3 is an example showing a voltage shift at 300° C. In FIG. 3, reference numeral (13) shows the current-voltage characteristics in the case of $N_2$ gas only. Reference numeral (12) shows a voltage shift of delta V (11) in current-voltage characteristics in the case in which 1000 ppm of $H_2$ gas is added thereto.

On the other hand, when an ohmic electrode capable of detecting the concentration of a gas containing a molecule having a hydrogen atom is formed on the surface of a p-type layer which in turn is formed on an n-type semiconductor, as shown in FIG. 4, the voltage shifts in a decreasing direction. FIG. 4 is an example showing a voltage shift at 500° C. In FIG. 4, reference numeral (15) shows the current-voltage characteristics in the case of $N_2$ gas only, whereas reference numeral (16) shows a voltage shift of delta V (14) in current-voltage characteristics in the case in which 50 ppm of $H_2$ gas is added thereto.

The semiconductor in which the pn junction is formed includes known materials such as Si, and also compound semiconductors and the like, such as SiC, GaAs and the like. Further, the "semiconductor" referred to herein denotes not only an Si semiconductor but also a compound semiconductor. The semiconductor wafer is preferably a single crystal; however, as long as appropriate diode characteristics can be obtained, a polycrystalline material prepared by techniques such as chemical vapor deposition (CVD) and the like may be used.

In order to obtain a stable sensor output at a high temperature of 150° C. to 600° C. as an application temperature, it is preferable to use a semiconductor having the largest band gap possible. Particularly, SiC which has an excellent breakdown voltage, response time and the like compared with Si is preferably used. The SiC wafer is preferably a single crystal wafer having a high purity having the fewest possible defects such as a micropipe, dislocation or the like. At present, ordinarily, an n-type SiC wafer is less expensive than a p-type SiC wafer so that it is possible to decrease production cost of the gas sensor by using the n-type SiC wafer rather than the p-type SiC wafer. When a SiC wafer is selected as the semiconductor, it is preferable to form an epitaxial layer on a surface of at least one side of the wafer. By forming an epitaxial layer beforehand to fill a defect, such as a micropipe, polishing scratch and the like, of the wafer, a gas sensor which prevents generation of leakage current at the pn junction and which has high reliability can be obtained. The pn junction diode-type gas sensor of the present invention can be formed having, for example, a multi-layer type, a planar type, a mesa type and the like configuration. FIGS. 1 and 2 show examples of a multi-layer type sensor. FIGS. 11 and 12 show examples of a mesa type sensor. In the case of the mesa type sensor, it is preferable to provide a recess (for example, 920 in FIG. 11 and 921 in FIG. 12) between electrodes with the planar type as a base by utilizing a mesa etching technique. This is because generation of leakage current flowing on the surface thereof can effectively be prevented. Further, these figures are shown only for the purpose of explanation; however, the gas sensor of the present invention is by no means limited to dimension ratios or any relation of size among the respective components shown in these figures.

A lower limit value of the thickness of the epitaxial layer is preferably 1 μm or more, more preferably 3 μm or more, and furthermore preferably 5 μm or more. Such thicknesses can effectively prevent the generation of leakage current.

There is no theoretical limitation on an upper limit of the thickness of the epitaxial layer; however, from the standpoint of production efficiency, the thickness is preferably 20 µm or less, more preferably 15 µm or less, and furthermore preferably 10 µm or less.

A known technique can be used to form the pn junction. An electrical conductive-type layer differing from the semiconductor wafer to be used may be formed using an ion implantation method, or a doping method utilizing an excimer laser. For example, when an n-type semiconductor substrate is used, a region in which the electrical conductive type has become a p-type by doping can be obtained. When this region is designated as a "first semiconductor layer", the region other than this region which is occupied by the n-type semiconductor substrate is designated as the "second semiconductor layer". On the other hand, when a p-type semiconductor substrate is used, a region in which the electrical conductive type is converted to an n-type by doping can be obtained. When this region is designated as a "first semiconductor layer", the region other than this region which is occupied by the n-type semiconductor substrate is designated as the "second semiconductor layer". Further, it has already been described that the direction of the voltage shift obtained in correspondence with a gas concentration is changed by changing one combination of the p-type and the n-type to another combination thereof.

As long as the ohmic electrode for use in the gas sensor of the present invention can obtain an ohmic contact, the material thereof is not particularly limited; it is preferable from a standpoint of practical application to select an electrode having excellent heat resistance as the gas sensor. Examples of the ohmic electrode for the p-type semiconductor include metal elements, mixtures, compounds, alloys, multi-layers and the like such as Al, Ti/Al ("Ti/Al" here refers to an electrode in which Ti and Al are deposited in this order on a surface of the semiconductor. Hereinafter, the convention as above applies to electrodes other than Ti/Al), Al/Ni, PtSi$_x$ (platinum silicide), TaSi$_x$ (tantalum silicide) and the like. When the gas sensor of the present invention is used in an ambient exposed to a high temperature of 500° C. or more, it is particularly preferable from a standpoint of heat resistance to use a silicide such as PtSi$_x$ (platinum silicide), TaSi$_x$ (tantalum silicide) or the like. On the other hand, examples of the ohmic electrode for the n-type semiconductor include metal elements, compounds, mixtures, alloys, multi-layers and the like such as Ta, Ni, Ti/W, Ni/Ti/W, NiSi$_x$ (nickel silicide), TaSi$_x$ (tantalum silicide), WSi$_x$ (tungsten silicide) and the like. These ohmic electrodes for the n-type semiconductor each have excellent heat resistance and can be used in an ambient exposed to a high temperature of 500° C. or more. Silicides are ordinarily non-stoichiometric compounds where the ratio between metal and silicon is expressed by x. When a silicide is used as the ohmic electrode, a portion of the silicide is decomposed, depending on the forming conditions of the electrode, to generate a mixture of silicide, metal and silicon. Even such a mixture can be used as the ohmic electrode of the gas sensor of the present invention, as long as the ohmic property is confirmed by measurement of its current-voltage characteristics.

These electrodes can be formed on a surface of the semiconductor by various types of techniques such as thermal evaporation, sputtering, laser ablation and the like; however, particularly when a silicide electrode is formed, it is desirable to deposit a target silicide by laser ablation and thereafter subject the thus deposited silicide to laser irradiation to enhance the adhesion thereof to the surface of the semiconductor. This secures a favorable ohmic property while preventing a composition misalignment.

On any one of the first ohmic electrode and the second ohmic electrode, a catalytic layer is formed containing a metallic catalytic component which dissociates a hydrogen atom from a molecule having the above-described hydrogen atom. The metallic catalytic component is not particularly limited, as long as it can dissociate hydrogen atom from the molecule having the hydrogen atom; however, it preferably contains platinum group element as an essential component. Specifically, examples of the components include Ru, Rh, Pd, Os, Ir and Pt. Such components are preferable since they can efficiently dissociate the hydrogen atom. Pt, Pd, Ir and Rh are particularly preferable among others. The catalytic layer is formed by a metallic element, an alloy, an oxide, or a compound of these platinum group elements; however, these platinum group elements can be used in a configuration in which they are carried by a porous dielectric thin film and the like. By using a porous material, surface area is increased to further enhance catalytic activity. As the porous dielectric thin film, films made of ceramics having excellent heat resistance such as γ-alumina, corundum, spinel, perovskite and the like are preferred. The configurations thereof are not particularly limited, as long as catalytic action is not lost which promotes dissociation of the hydrogen atom.

The thickness of the catalytic layer is preferably in a range of between 10 nm and 200 nm (more preferably between 30 nm and 150 nm, and furthermore preferably between 50 nm and 100 nm). When the thickness of the catalytic layer is less than 10 nm, formation of a polarization layer by the hydrogen atom becomes difficult whereupon sensor sensitivity is lowered. When the thickness of the catalytic layer is more than 200 nm, it takes much time for a dissociated hydrogen atom to reach an interface with the semiconductor such that the response of the gas sensor is lowered.

Figure 1:
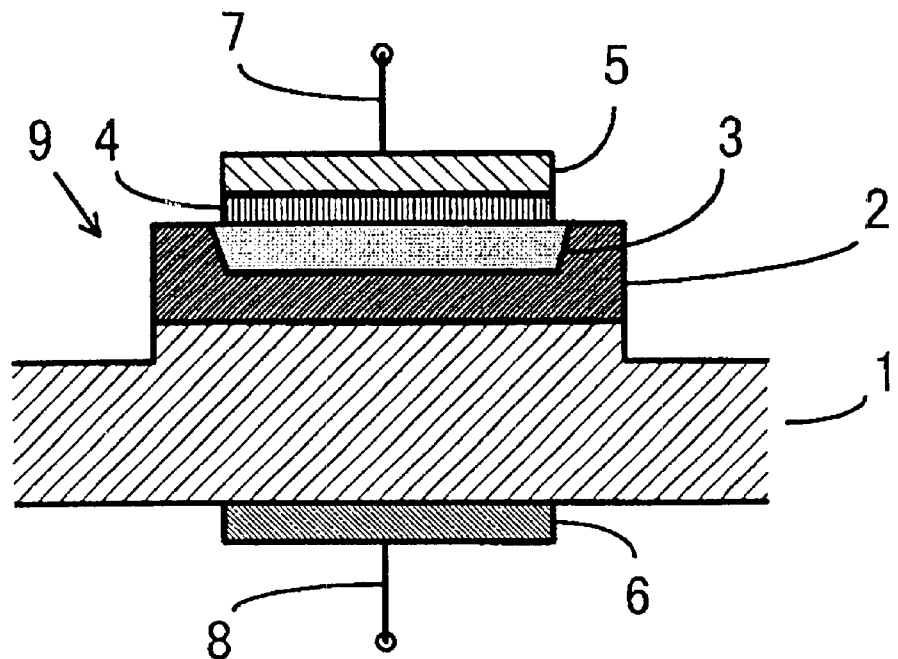
FIG. 1 is an explanatory view showing an aspect of a multi-layer type, pn junction diode-type gas sensor of the present invention using a p-type semiconductor.

DESCRIPTION OF SYMBOLS USED IN THE DRAWINGS 1, 110 . . . p-type semiconductor wafer
10, 111 . . . n-type semiconductor wafer
2, 210 . . . p-type epitaxial layer
20, 211 . . . n-type epitaxial layer
3, 310 . . . n-type doped region layer
30, 311 . . . p-type doped region layer
4, 410 . . . ohmic electrode for n-type
40, 411 . . . ohmic electrode for p-type
5, 50, 510, 511 . . . catalytic layer
6, 610 . . . ohmic electrode for p-type
60, 611 . . . ohmic electrode for n-type
7, 70, 8, 80, 710, 810, 711, 811 . . . lead-outline
9 . . . multi-layer type, pn junction diode-type gas sensor used in Example 1
90 . . . multi-layer type, pn junction diode-type gas sensor used in Example 2
910 . . . mesa-type, pn junction diode-type gas sensor using a p-type semiconductor
911 . . . mesa-type, pn junction diode-type gas sensor using an n-type semiconductor
920, 921 . . . recess formed by a mesa etching technique
11 . . . a voltage shift delta V to a high voltage side of the gas sensor of Example 1
12 . . . plots of the current-voltage characteristics shifted to the high voltage side of the gas sensor of Example 1
13 . . . plots of the current-voltage characteristics for $N_2$ gas of the gas sensor of Example 1
14 . . . a voltage shift delta V to a low voltage side of the gas sensor of Example 2
15 . . . plots of the current-voltage characteristics for $N_2$ gas of the gas sensor of Example 2
16 . . . plots of the current-voltage characteristics shifted to the low voltage side of the gas sensor of Example 2

EXAMPLES

The gas sensor according to the present invention is explained with reference to the embodiments illustrated below. However, the present invention should not be construed as being limited thereto.

Figure 2:
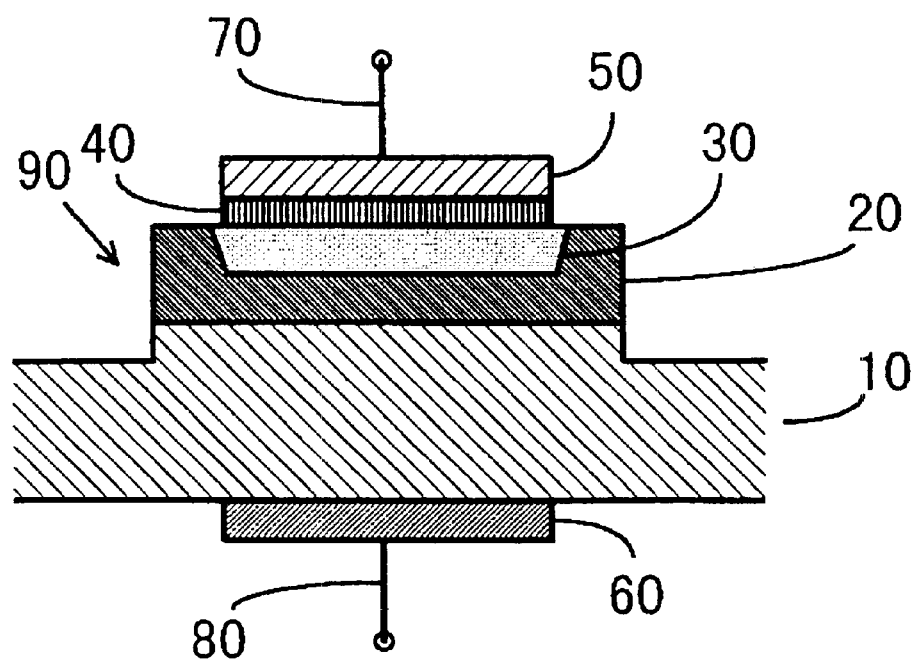
FIG. 2 is an explanatory view showing an aspect of a multi-layer type, pn junction diode-type gas sensor of the present invention using an n-type semiconductor.

Example 1 is an example in which a p-type SiC semiconductor wafer is used. The configuration of the gas sensor (9) of Example 1 is shown in FIG. 1. In FIG. 1, (1), (2), (3), (4), (5), (6), and (7) and (8) represent a p-type SiC semiconductor wafer, a previously formed p-type epitaxial layer, an n-type doped region layer, an ohmic electrode for an n-type, a catalytic layer, an ohmic electrode for a p-type, and schematic representations of lead-out lines, respectively. Example 2 is an example in which an n-type SiC semiconductor wafer is used. The configuration of the gas sensor (90) of Example 2 is shown in FIG. 2. In FIG. 2, (10), (20), (30), (40), (50), (60), and (70) and (80) represent an n-type SiC semiconductor wafer, a previously formed n-type epitaxial layer, a p-type doped region layer, an ohmic electrode for a p-type, a catalytic layer, an ohmic electrode for an n-type, and schematic representations of lead-out lines, respectively.

Example 1

On a surface of a p-type 4H—SiC wafer (Al doped amount: $1 \times 10^{18}/cm^3$; an epitaxial layer thereof being 10 μm thick and having an Al doped amount of $1.5 \times 10^{16}/cm^3$), $N^+$ ions were implanted in a predetermined site thereof in an amount of $1 \times 10^{15}/cm^2$ 30 keV by an ion implantation. Subsequently, the wafer was subjected to activation annealing in flowing Ar gas at 1500° C. for 30 minutes to prepare a pn junction SiC semiconductor.

On the other surface of the p-type wafer in which ions had not been implanted, Al was deposited and then irradiated with a KrF excimer laser under a condition of $1.0 J/cm^2 \times 100$ shots to form an Al ohmic electrode. On the other hand, on the n-type surface in which the ions had been implanted, a Ti ohmic electrode was formed using Ti by the same method as used to form the Al ohmic electrode.

On the Ti ohmic electrode formed on the n-type surface, Pt was deposited by thermal evaporation in vacuo to prepare a catalytic layer, thereby forming a multi-layer electrode composed of Al and Pt. Pt wire was welded to each electrode to monitor signals from the electrode. Thus, the desired gas sensor was prepared.

Using the thus obtained gas sensor, sensor sensitivity to various types of sample gases shown below was measured. The measuring conditions are described below.

Measuring Conditions

Figure 3:
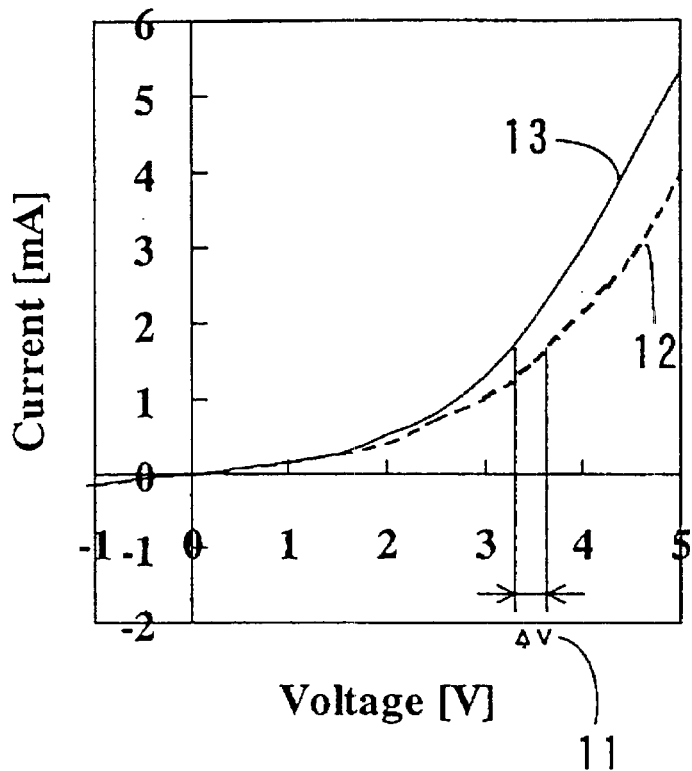
FIG. 3 is an explanatory view showing a voltage shift when an ohmic electrode is formed on a surface of an n-type layer formed on the p-type semiconductor.
Figure 5:
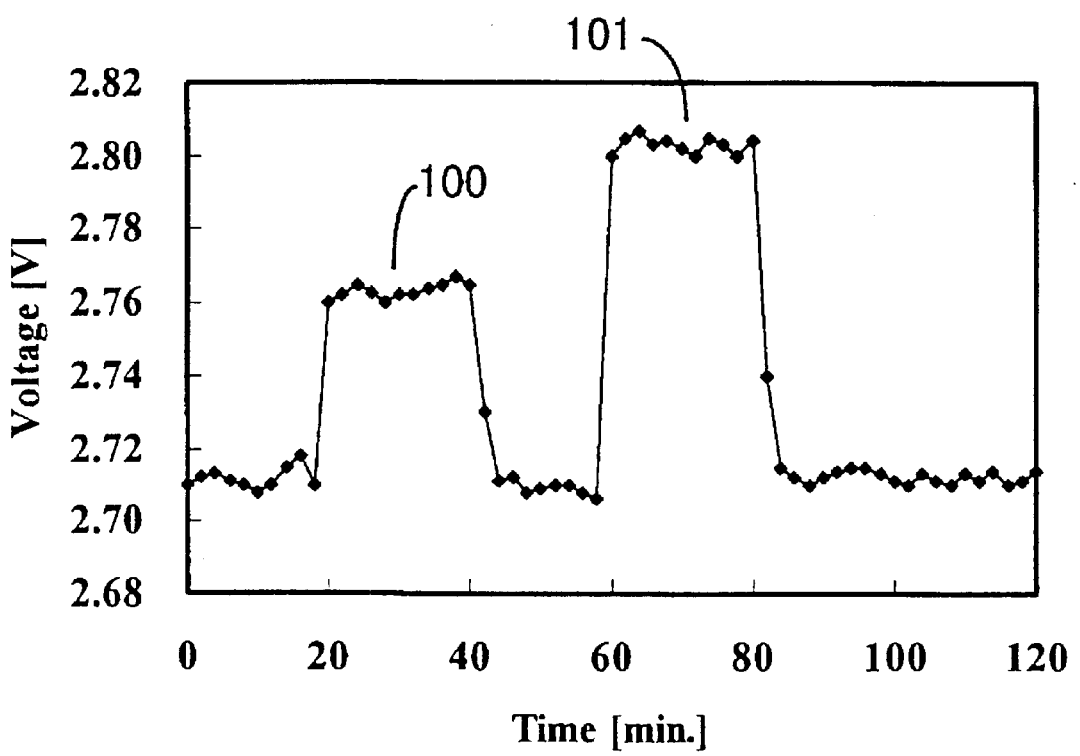
FIG. 5 is an explanatory view showing a measurement result of current voltage characteristics of a sample gas containing NH$_3$ of the gas sensor of Example 1 using the p-type semiconductor.
Figure 6:
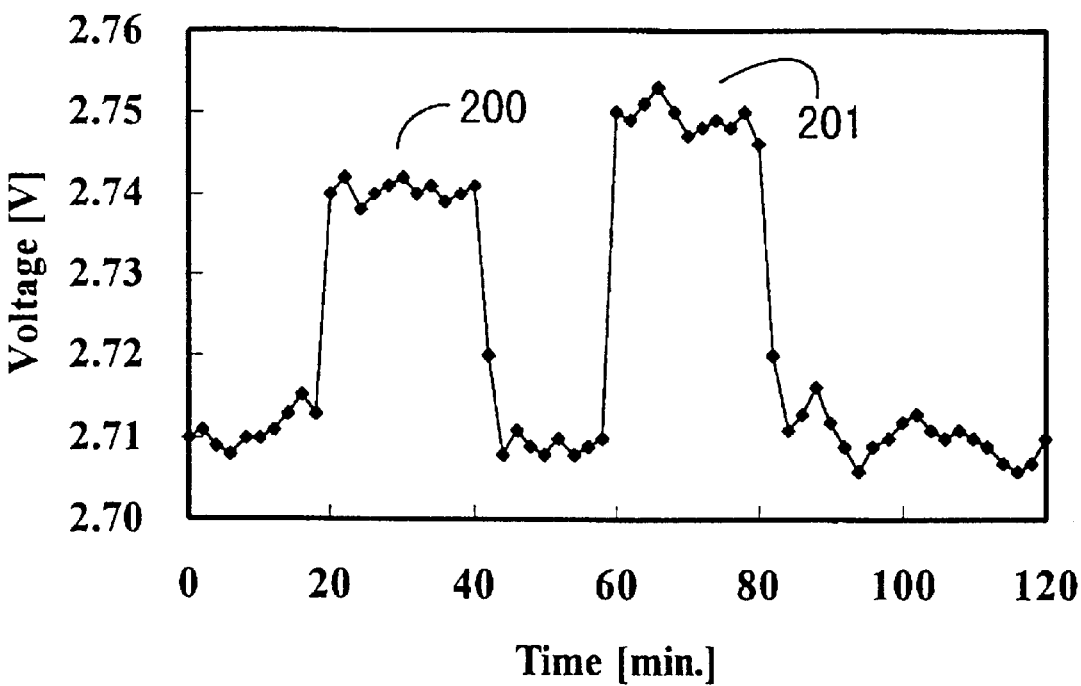
FIG. 6 is an explanatory view showing a measurement result of current-voltage characteristics of a sample gas containing C$_3$H$_6$ of the gas sensor of Example 1 using a p-type semiconductor.
Figure 7:
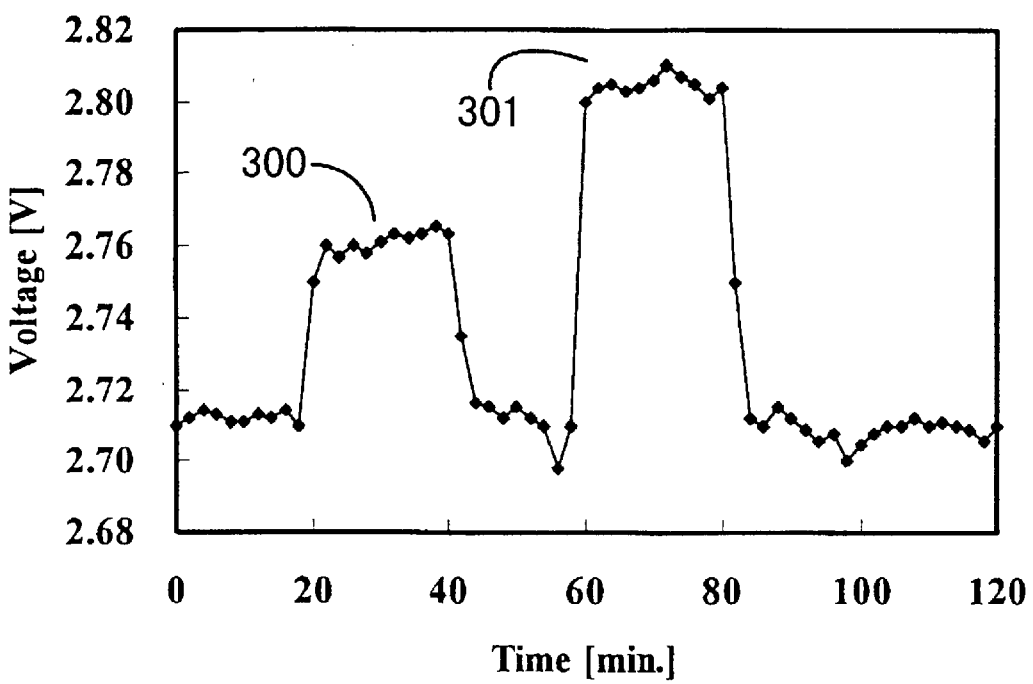
FIG. 7 is an explanatory view showing a measurement result of current-voltage characteristics of a sample gas containing H$_2$ of the gas sensor of Example 1 using a p-type semiconductor.

Applied current: 1 mA
Element temperature: 300° C.
Flow rate of sample gas: 15 slm (The flow rate is 15 liters per minute under standard conditions).
Sample gas types: $H_2$, $NH_3$, and $C_3H_6$
Sample gas concentration: 100 to 5000 ppm
Base gas: $N_2$ FIG. 3 shows a measurement result of current-voltage characteristics of a sample gas containing $H_2$ in an amount of 1000 ppm. The voltage was shifted to a high voltage side (in FIG. 3, a shift from (13) to (12) by delta V), thereby enabling detection of $H_2$. Further, FIG. 5 shows a measurement result of current-voltage characteristics of a sample gas containing $NH_3$. In FIG. 5, a peak (100) on the left-hand side represents an $NH_3$ concentration of 500 ppm, while another peak (101) on the right-hand side represents an $NH_3$ concentration of 1000 ppm. Thus, an output voltage was obtained in accordance with the concentration of $NH_3$. FIG. 6 shows a measurement result of current-voltage characteristics of a sample gas containing $C_3H_6$. In FIG. 6, a peak (200) on the left-hand side represents a $C_3H_6$ concentration of 100 ppm, while another peak (201) on the right-hand side represents a $C_3H_6$ concentration of 150 ppm. Thus, an output voltage was obtained in accordance with the concentration of $C_3H_6$. FIG. 7 shows a measurement result of current-voltage characteristics of a sample gas containing $H_2$. In FIG. 7, a peak (300) on the left-hand side represents a $H_2$ concentration of 1000 ppm, while another peak (301) on the right-hand side represents a $H_2$ concentration of 5000 ppm. Thus, an output voltage was obtained in accordance with the concentration of $H_2$. The above results demonstrate that the gas sensor of the present invention has sensitivity corresponding to the concentration of gases containing a molecule having a hydrogen atom.

Example 2

On a surface of an n-type 6H—SiC wafer (N doped amount: $1.9 \times 10^{18}/cm^3$; an epitaxial layer thereof being 10 µm thick and having an N doped amount of $1.5 \times 10^{16}/cm^3$), Al ions were implanted by an excimer laser doping method to prepare a pn junction SiC semiconductor. On this occasion, the Al ion had a concentration gradient such that the amount of Al ions implanted on a surface portion of the wafer was $1 \times 10^{21}/cm^3$, and the amount of Al ions implanted at a depth of 60 nm from the surface was $1 \times 10^{16}/cm^3$.

On the other n-type surface in which ions were not implanted, Ni was deposited by thermal evaporation in vacuo and then heat treated in flowing $H_2$ gas at 1000° C. for 5 minutes to form an Ni ohmic electrode. On the other hand, on the p-type surface in which the ions were implanted, Al was deposited by thermal evaporation in vacuo to form an Al ohmic electrode. Further, on the thus formed Al ohmic electrode, Pt was sputtered by a DC magnetron sputtering to prepare a catalytic layer thereby forming a multi-layer electrode composed of Al and Pt. A Pt wire was welded to each electrode to monitor signals from the electrode. Thus, the desired gas sensor was prepared.

Using the thus obtained gas sensor, sensor sensitivity to various types of sample gases shown below was measured. The measuring conditions are described below.

Measuring Conditions

Figure 4:
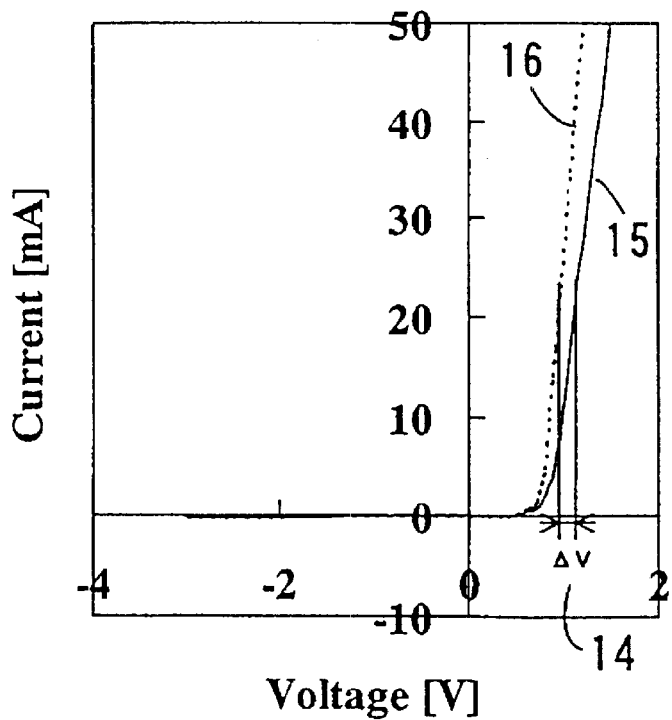
FIG. 4 is an explanatory view showing a voltage shift when an ohmic electrode is formed on a surface of a p-type layer formed on the n-type semiconductor.
Figure 8:
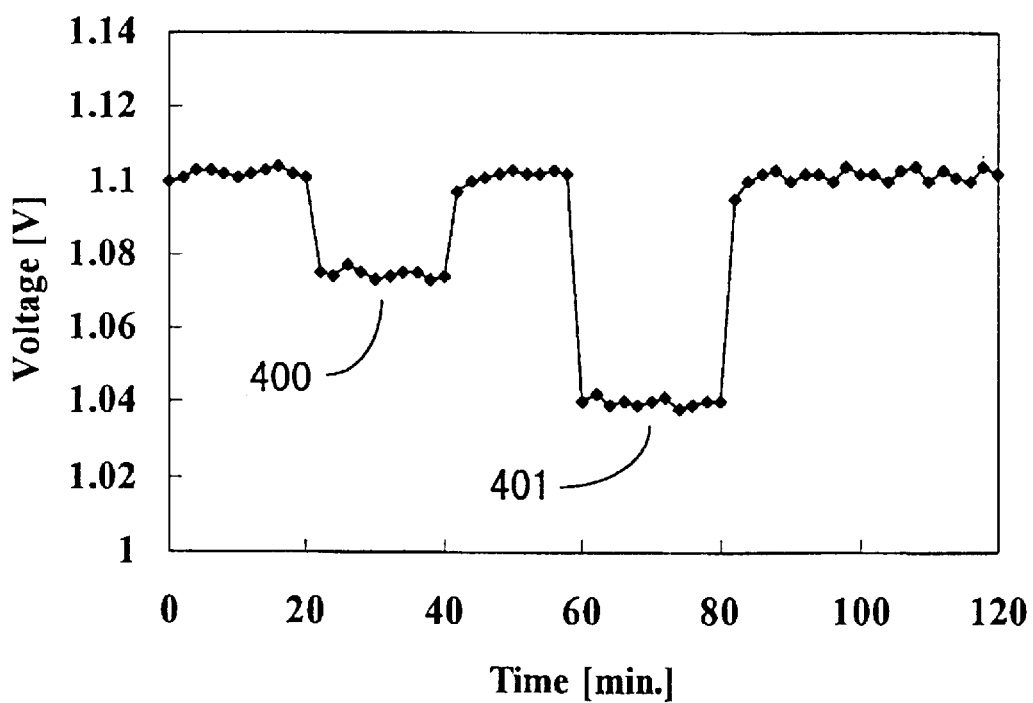
FIG. 8 is an explanatory view showing a measurement result of current-voltage characteristics of a sample gas containing NH$_3$ of the gas sensor of Example 2 using a n-type semiconductor.
Figure 9:
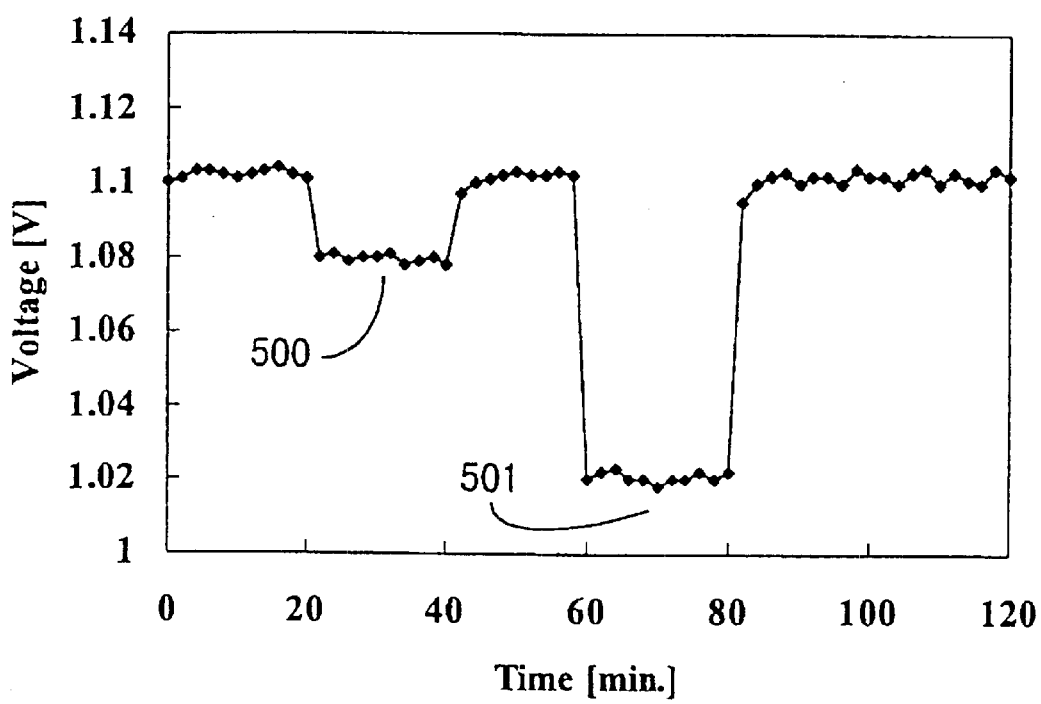
FIG. 9 is an explanatory view showing a measurement result of current-voltage characteristics of a sample gas containing $C_3H_6$ of the gas sensor of Example 2 using a n-type semiconductor.
Figure 10:
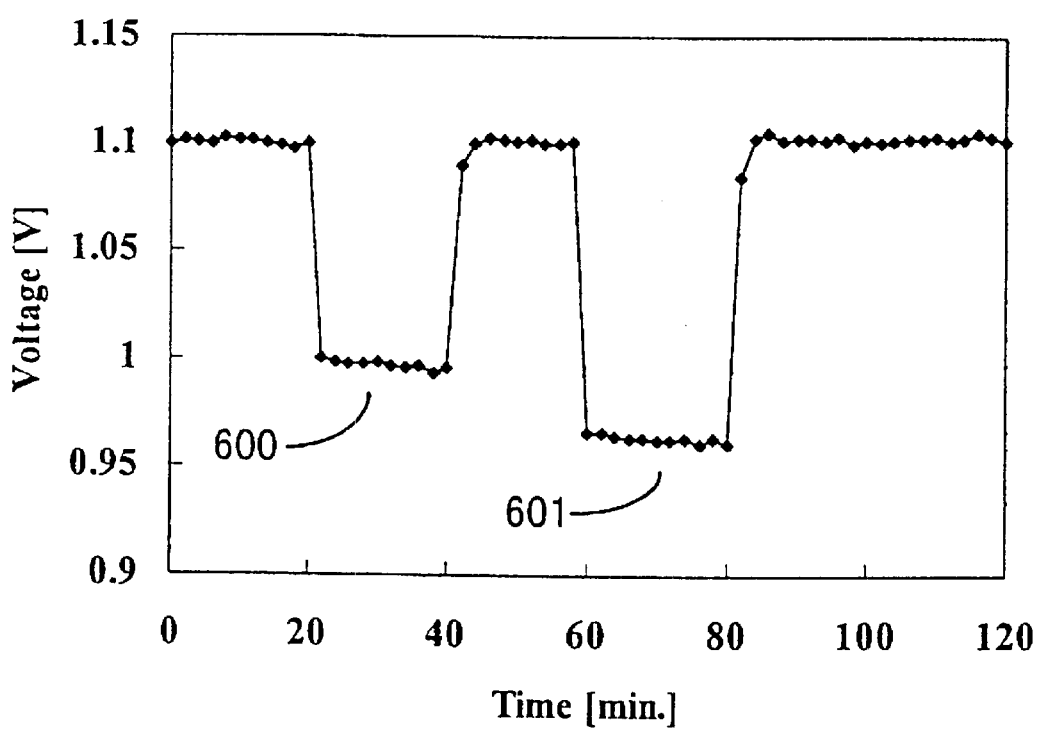
FIG. 10 is an explanatory view showing a measurement result of current-voltage characteristics of a sample gas containing $H_2$ of the gas sensor of Example 2 using a n-type semiconductor.
Figure 11:
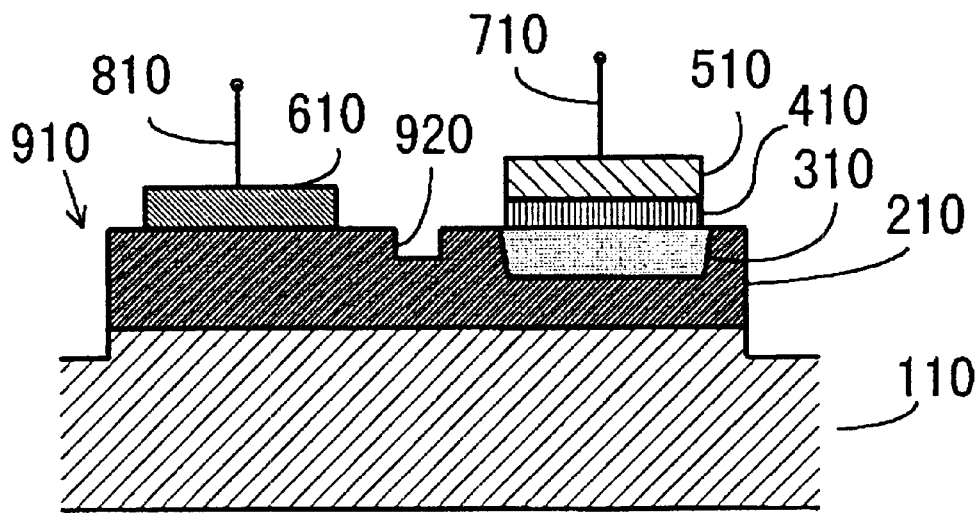
FIG. 11 is an explanatory view showing an aspect of a mesa-type, pn junction diode-type gas sensor of the present invention using a p-type semiconductor.
Figure 12:
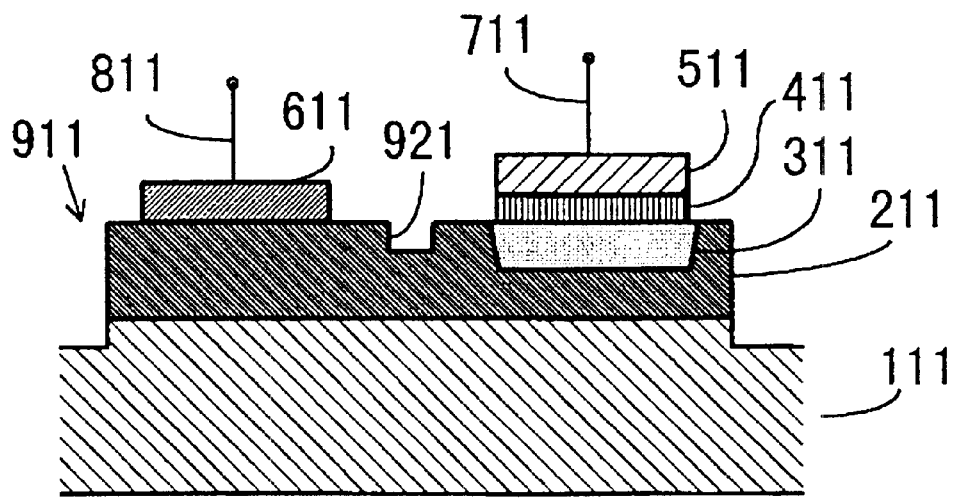
FIG. 12 is an explanatory view showing an aspect of a mesa-type, pn junction diode-type gas sensor of to the present invention using a n-type semiconductor.

Applied current: 20 mA
Element temperature: 500° C.
Flow rate of sample gas: 15 slm (The flow rate was 15 liters per minute under standard conditions.)
Sample gas types: $H_2$, $NH_3$, and $C_3H_6$
Sample gas concentration: 2 to 100 ppm
Base gas: $N_2$ FIG. 4 shows a measurement result of current-voltage characteristics of a sample gas containing $H_2$ of 50 ppm. The voltage shifted to a low voltage side (in FIG. 4, a shift from (15) to (16)) thereby enabling detection of $H_2$. Further, FIG. 8 shows a measurement result of current-voltage characteristics of a sample gas containing $NH_3$. In FIG. 8, a peak (400) on the left-hand side of FIG. 8 represents an $NH_3$ concentration of 20 ppm, while another peak (401) on the right-hand side of FIG. 8 represents an $NH_3$ concentration of 100 ppm. Thus, the output voltage was obtained in accordance with the concentration of $NH_3$. In FIG. 9, a measurement result of current-voltage characteristics of a sample gas containing $C_3H_6$ is shown. In FIG. 9, a peak (500) on the left-hand side of FIG. 9 represents a $C_3H_6$ concentration of 2 ppm, while another peak (501) on the right-hand side of FIG. 9 represents a $C_3H_6$ concentration of 10 ppm. Thus, an output voltage was obtained in accordance with the concentration of $C_3H_6$. FIG. 10 shows a measurement result of current-voltage characteristics of a sample gas containing $H_2$. In FIG. 10, a peak (600) on the left-hand side represents a $H_2$ concentration of $_{50}$ ppm, while another peak (601) on the right-hand side represents a $H_2$ concentration of 100 ppm. Thus, an output voltage was obtained in accordance with the concentration of $H_2$. Further, since Example 2 is in a reverse relation with Example 1 with respect to the pn type, the direction of the output signal is opposite that of Example 1. The above results demonstrate that the gas sensor of the present invention has sensitivity corresponding to the gas concentration of gases containing a molecule having a hydrogen atom.

Example 3

Figure 13:
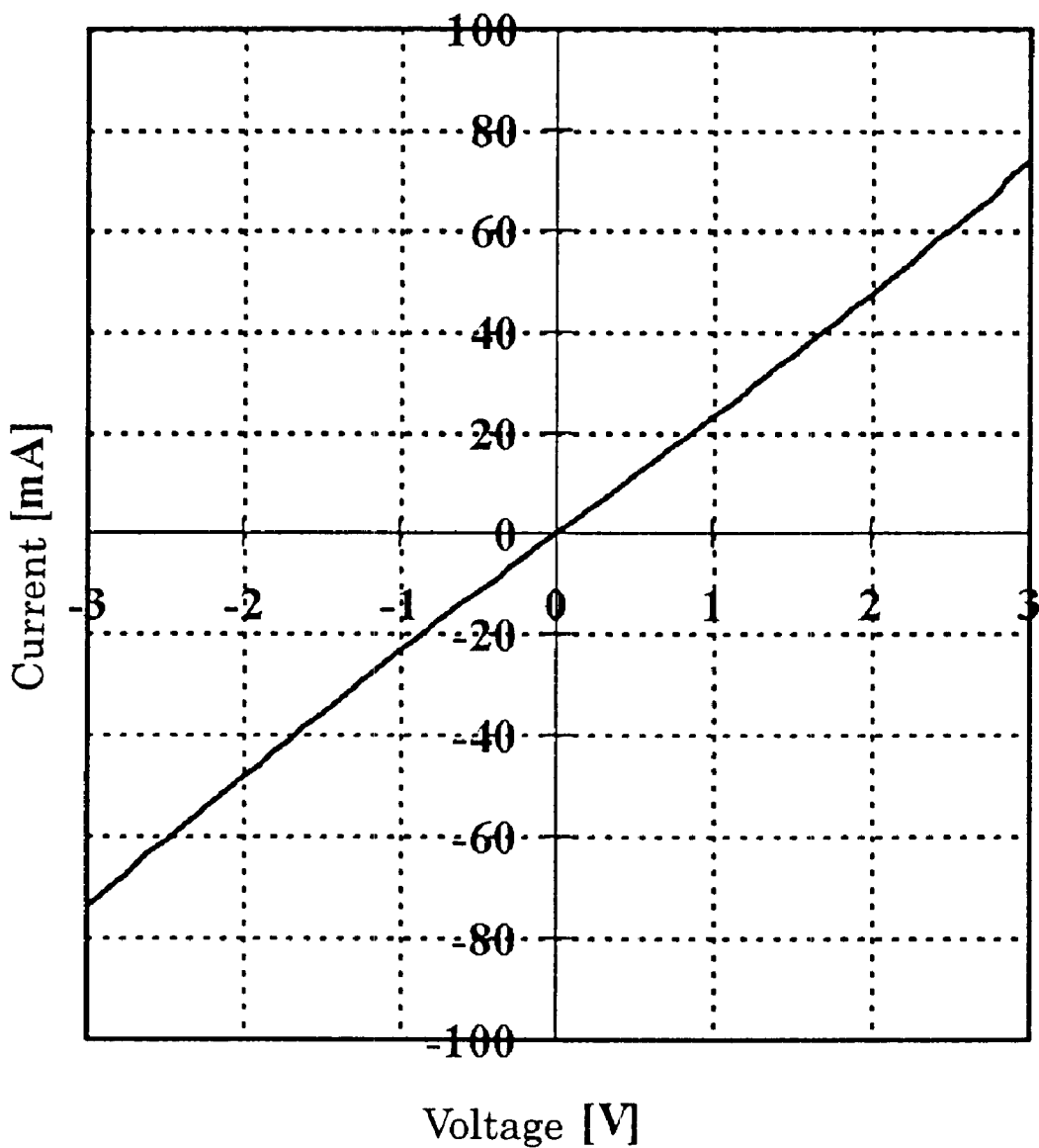
FIG. 13 shows current (I)-voltage (V) characteristics of a $TaSi_x$ electrode (x=2) formed on the surface of an n-type 6H—SiC wafer.
Figure 14:
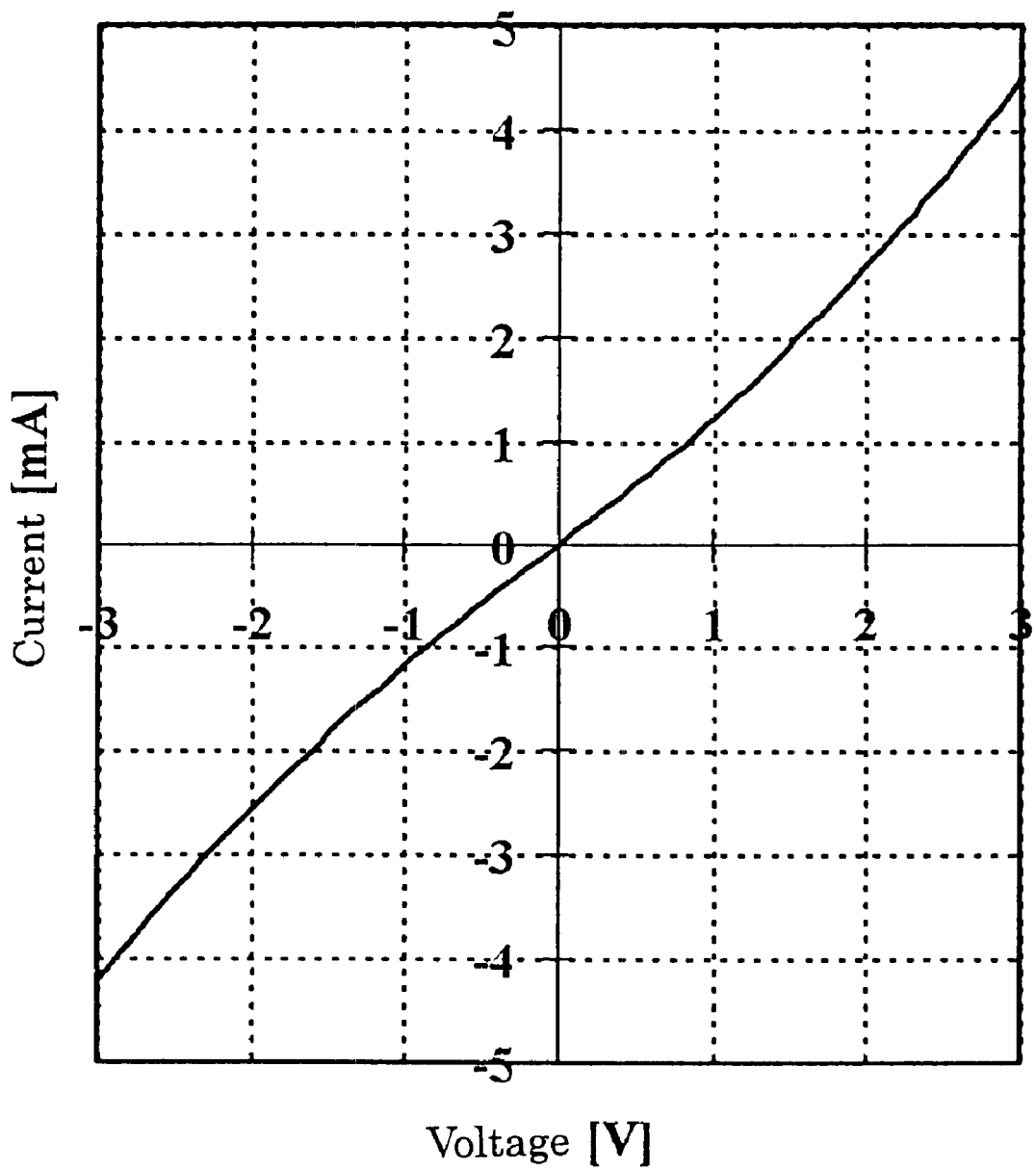
FIG. 14 shows current (I)-voltage (V) characteristics of $TaSi_x$ electrode (x=2) formed on the surface of a p-type 6H—SiC wafer.

On a surface of an n-type or a p-type 6H—SiC wafer, $TaSi_x$ (x=2) was deposited in a thickness of about 30 nm by laser ablation and, subsequently, irradiated by an excimer laser (KrF 248 nm, τp=20 ns) for 100 pulses under an energy irradiation density of 1.0 J/cm². Thereafter, $TaSi_x$ was further deposited in a thickness of about 70 nm to prepare an electrode. FIGS. 13 and 14 show the respective current (I)–voltage (V) characteristics of electrodes prepared on the n-type and p-type 6H—SiC wafers. Thus, FIGS. 13 and 14 confirm that $TaSi_x$ can be used as an ohmic electrode for either n-type or p-type configurations.

According to the present invention, when either Si single crystal or SiC single crystal is employed, a gas sensor having a simple constitution, exhibiting a small change in diode characteristics with time in long-term service, and having sensitivity to a molecule having a hydrogen atom, for example, $H_2$, $NH_3$, $H_2S$, a hydrocarbon and the like, can be obtained.

It should further be apparent to those skilled in the art that various changes in form and detail of the invention as shown and described above may be made. It is intended that such changes be included within the spirit and scope of the claims appended hereto.

This application is based on Japanese Patent Application Nos. 2000-242029, filed Aug. 10, 2000 and 2000-374551, filed Dec. 8, 2000, the disclosures of which are incorporated herein by reference in their entirety.

What is claimed is:

1. A pn junction diode gas sensor comprising:
   a first semiconductor layer which is either a p-type or n-type semiconductor layer;
   a second semiconductor layer of a type different from said first semiconductor layer;
   a semiconductor substrate on which said first semiconductor layer and said second semiconductor layer are disposed;
   a first ohmic electrode in electrical contact with said first semiconductor layer;
   a second ohmic electrode in electrical contact with said second semiconductor layer; and
   a catalytic layer disposed on one of said first ohmic electrode and said second ohmic electrode, said catalytic layer containing a metallic catalytic component which dissociates hydrogen atom from a molecule having hydrogen atom in contact with the catalytic layer,
   wherein at least one of said first and second semiconductor layers is formed as an epitaxial layer on a surface of said semiconductor substrate.

2. The pn junction diode gas sensor as claimed in claim 1, wherein said metallic catalytic component comprises a platinum group metal.

3. The pn junction diode gas sensor as claimed in claim 2, wherein the platinum group metal is selected from the group consisting of Ru, Rh, Pd, Os, Ir, Pt and mixtures thereof.

4. The pn junction diode-type gas sensor as claimed in claim 1, wherein said first and second semiconductor layers comprise a compound semiconductor.

5. The pn junction diode-type gas sensor as claimed in claim 1, wherein at least one of said first and second ohmic electrodes comprises a silicide.

6. The pn junction diode-type gas sensor as claimed in claim 1, wherein the catalytic layer has a thickness of 10–200 nm.

7. The pn junction diode gas sensor as claimed in claim 1, wherein the has a thickness of 1–20 micrometers.

8. The pn junction diode gas sensor as claimed in claim 5, wherein said silicide is selected from the group consisting of $PtSi_x$, $TaSi_x$, $NiSi_x$, $WSi_x$ and mixtures thereof.

* * * * *